US010391262B2

(12) United States Patent
Durvasula et al.

(10) Patent No.: US 10,391,262 B2
(45) Date of Patent: Aug. 27, 2019

(54) REMOVABLE ACTUATING CAP FOR USE WITH AN AUTO-INJECTOR ASSEMBLY

(71) Applicant: Windgap Medical, Inc., Watertown, MA (US)

(72) Inventors: Ashritha Durvasula, Cambridge, MA (US); Mary Carter, Boston, MA (US); Jeffrey Thomas Chagnon, Somerville, MA (US); Cole Constantineau, Cambridge, MA (US); Chris Stepanian, Somverville, MA (US); Adam Standley, Boston, MA (US); Brent Buchine, Austin, TX (US)

(73) Assignee: Windgap Medical, Inc., Watertown, MA (US)

( * ) Notice: Subject to any disclaimer, the term of this patent is extended or adjusted under 35 U.S.C. 154(b) by 308 days.

(21) Appl. No.: 15/099,431

(22) Filed: Apr. 14, 2016

(65) Prior Publication Data
US 2016/0220764 A1    Aug. 4, 2016

Related U.S. Application Data

(63) Continuation-in-part of application No. 14/218,355, filed on Mar. 18, 2014, now Pat. No. 9,199,037.

(60) Provisional application No. 62/147,958, filed on Apr. 15, 2015, provisional application No. 62/204,904, filed on Aug. 13, 2015.

(51) Int. Cl.
*A61M 5/32* (2006.01)
*A61M 5/315* (2006.01)
*A61M 5/19* (2006.01)
*A61M 5/20* (2006.01)

(52) U.S. Cl.
CPC ............ *A61M 5/3202* (2013.01); *A61M 5/19* (2013.01); *A61M 5/2033* (2013.01); *A61M 5/2066* (2013.01); *A61M 5/31596* (2013.01); *A61M 2005/202* (2013.01); *A61M 2005/206* (2013.01)

(58) Field of Classification Search
CPC ...... A61M 2005/202; A61M 2005/206; A61M 5/19; A61M 5/2033; A61M 5/2066; A61M 5/31596; A61M 5/3202
See application file for complete search history.

(56) References Cited

U.S. PATENT DOCUMENTS

| 3,680,558 | A | 8/1972 | Kapelowitz |
| 3,946,732 | A | 3/1976 | Hurscham |
| 4,031,892 | A | 6/1977 | Hurschman |
| 4,060,082 | A | 11/1977 | Lindberg et al. |
| 4,529,403 | A | 7/1985 | Kamstra |
| 4,643,721 | A | 2/1987 | Brunet |
| 4,755,169 | A | 7/1988 | Sarnoff et al. |

(Continued)

FOREIGN PATENT DOCUMENTS

| EP | 961612 B1 | 4/2009 |
| WO | WO9208506 A1 | 5/1992 |

(Continued)

*Primary Examiner* — Imani Hayman
(74) *Attorney, Agent, or Firm* — Ascentage Patent Law, LLC; Travis Lee Johnson; David S. Einfeldt

(57) ABSTRACT

A removable cap for use with an auto-injector device, whereupon removal of the cap triggers an actuating assembly that can cause an automatic mixing of medicament components in an auto-injector device and/or place the auto-injector in a state to be used.

22 Claims, 13 Drawing Sheets

(56) References Cited

U.S. PATENT DOCUMENTS

| | | |
|---|---|---|
| 5,360,410 A | 11/1994 | Wacks |
| 5,569,193 A | 10/1996 | Hofstetter et al. |
| 5,704,918 A | 1/1998 | Higashikawa |
| 5,899,881 A | 5/1999 | Grimard et al. |
| 6,149,628 A | 11/2000 | Szapiro et al. |
| 6,309,372 B1 | 10/2001 | Fischer et al. |
| 6,641,561 B1 | 11/2003 | Hill et al. |
| 6,656,150 B2 | 12/2003 | Hill et al. |
| 6,770,052 B2 | 8/2004 | Hill et al. |
| 6,852,103 B2 | 2/2005 | Fowles et al. |
| 7,449,012 B2 | 11/2008 | Young et al. |
| 7,621,887 B2 | 11/2009 | Griffiths et al. |
| 7,749,190 B2 | 7/2010 | Griffiths et al. |
| 7,947,742 B2 | 5/2011 | Batycky et al. |
| 8,057,427 B2 | 11/2011 | Griffiths et al. |
| 8,251,947 B2 | 8/2012 | Kramer et al. |
| 8,613,720 B2 | 12/2013 | Bendek et al. |
| RE44,847 E | 4/2014 | Sadowski et al. |
| 8,696,618 B2 | 4/2014 | Kramer et al. |
| 2002/0046563 A1 | 2/2002 | Hill et al. |
| 2002/0042592 A1 | 4/2002 | Wilmot et al. |
| 2002/0049406 A1 | 4/2002 | Hill et al. |
| 2002/0049407 A1 | 4/2002 | Hill et al. |
| 2005/0074498 A1 | 4/2005 | Tarara et al. |
| 2005/0148933 A1 | 7/2005 | Raven et al. |
| 2005/0177100 A1 | 8/2005 | Harper et al. |
| 2006/0079834 A1 | 4/2006 | Tennican et al. |
| 2007/0116729 A1 | 5/2007 | Palepu |
| 2007/0202163 A1 | 8/2007 | Rawas-Qalaji et al. |
| 2007/0293582 A1 | 12/2007 | Hill |
| 2008/0103490 A1 | 5/2008 | Edwards et al. |
| 2008/0281271 A1 | 11/2008 | Griffiths et al. |
| 2009/0171311 A1 | 7/2009 | Genosar et al. |
| 2010/0228190 A1 | 9/2010 | Griffiths et al. |
| 2010/0318035 A1 | 12/2010 | Edwards et al. |
| 2011/0092906 A1 | 4/2011 | Bottger et al. |
| 2011/0237681 A1 | 9/2011 | Patycky et al. |
| 2012/0179137 A1 | 7/2012 | Bartlett et al. |
| 2012/0302989 A1 | 11/2012 | Kramer et al. |
| 2013/0018310 A1 | 1/2013 | Boyd et al. |
| 2013/0023822 A1 | 1/2013 | Edwards et al. |
| 2013/0060232 A1 | 3/2013 | Adlon et al. |
| 2013/0018313 A1 | 7/2013 | Kramer et al. |
| 2013/0178823 A1 | 7/2013 | Buchine et al. |
| 2013/0274707 A1 | 10/2013 | Wilmont et al. |
| 2013/0317477 A1 | 11/2013 | Edwards et al. |
| 2014/0243741 A1 * | 8/2014 | Kaufmann .......... A61M 5/2066 604/88 |
| 2014/0276385 A1 | 9/2014 | Buchine et al. |
| 2015/0174323 A1 | 6/2015 | Edwards et al. |
| 2015/0367073 A1 | 12/2015 | Standley et al. |
| 2015/0374925 A1 | 12/2015 | Standley et al. |
| 2016/0220764 A1 | 4/2016 | Durvasula et al. |

FOREIGN PATENT DOCUMENTS

| | | |
|---|---|---|
| WO | WO2008114035 A1 | 9/2008 |
| WO | WO2008154092 A1 | 12/2008 |
| WO | WO2005032523 A2 | 1/2009 |
| WO | WO2009118754 A2 | 10/2009 |
| WO | WO2010068415 A1 | 6/2010 |
| WO | WO2011060541 A1 | 5/2011 |
| WO | WO2011109340 A1 | 9/2011 |
| WO | WO2012090168 A1 | 5/2012 |
| WO | WO2012099898 A2 | 7/2012 |
| WO | WO2013063707 A1 | 5/2013 |

* cited by examiner

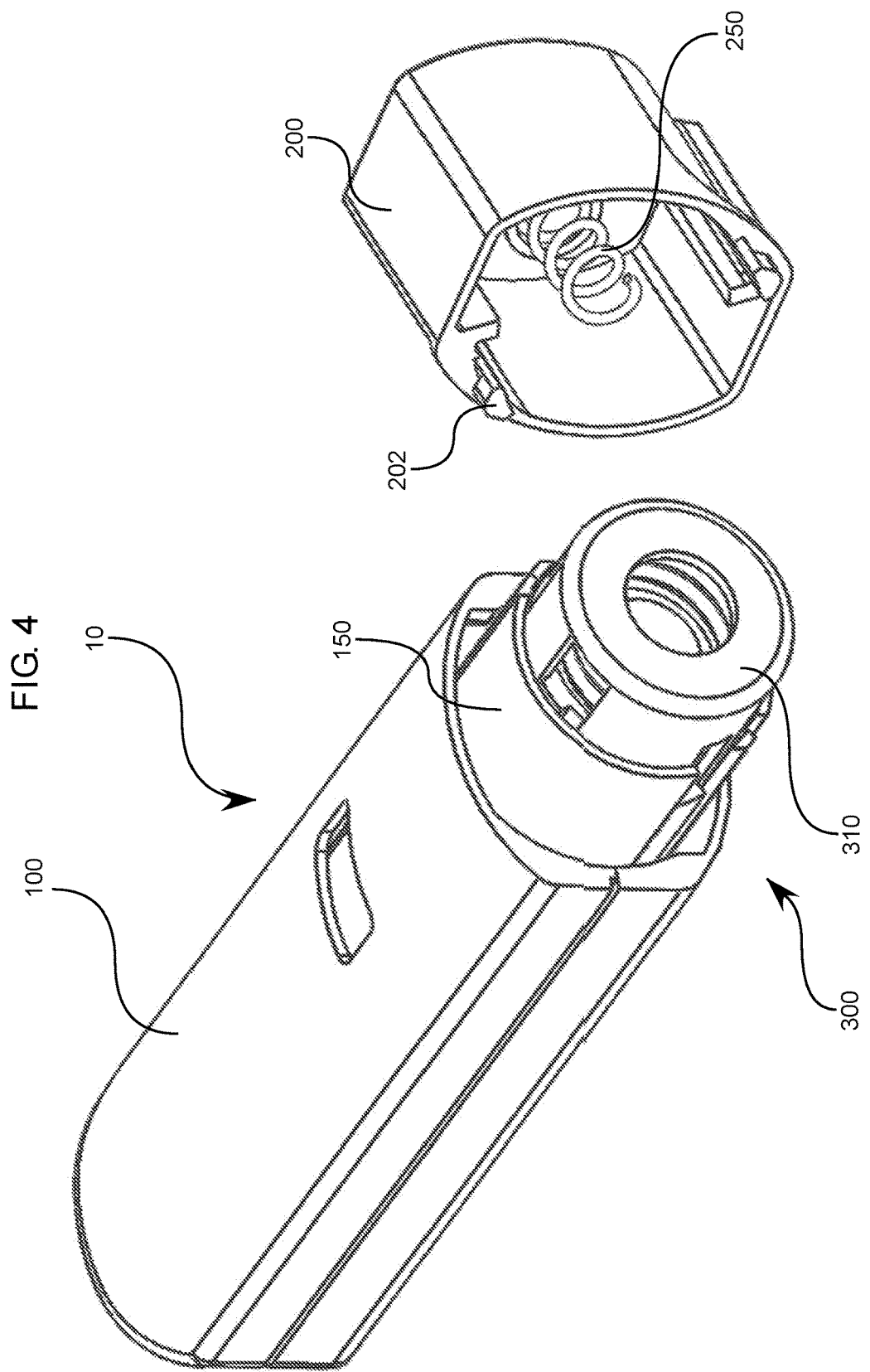

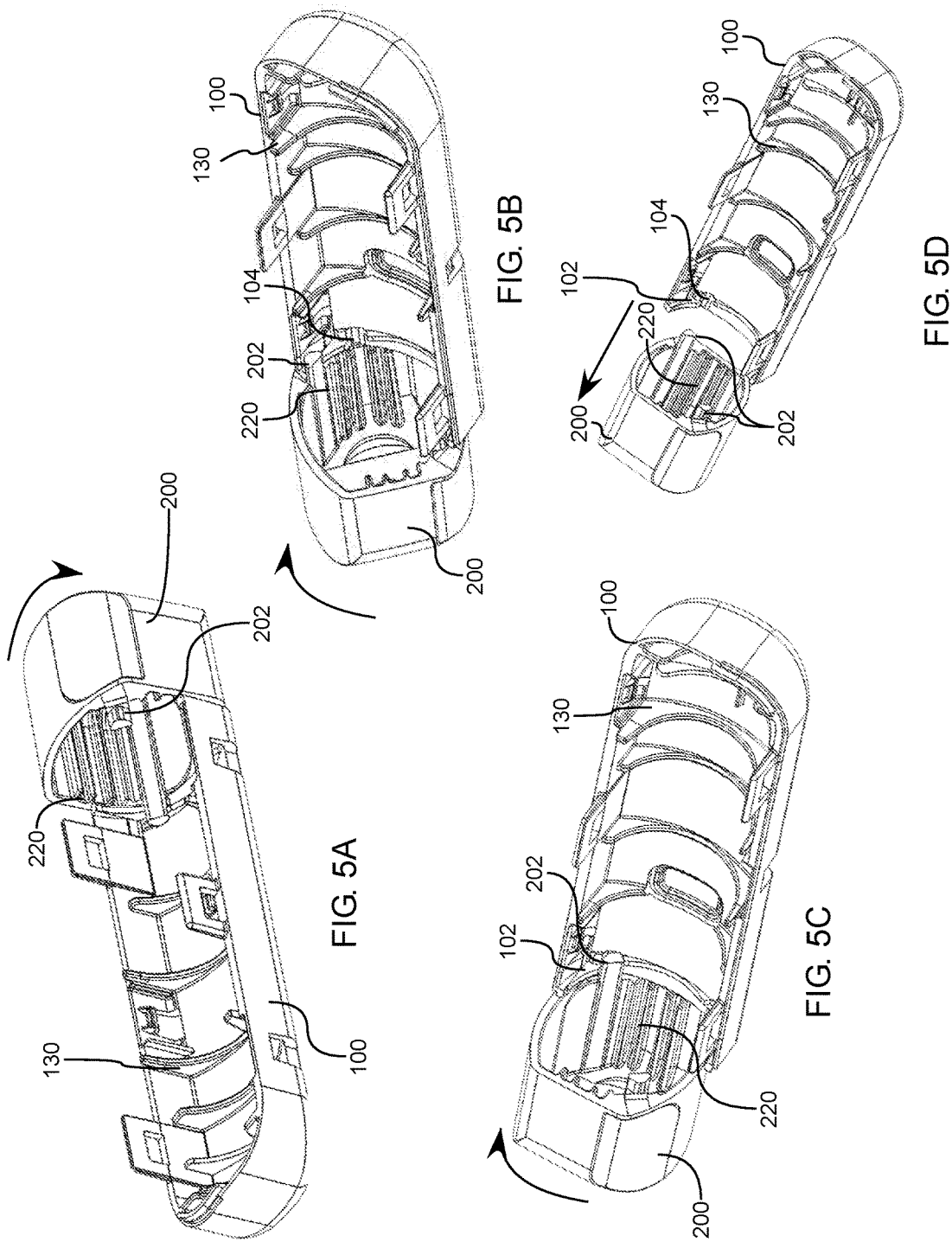

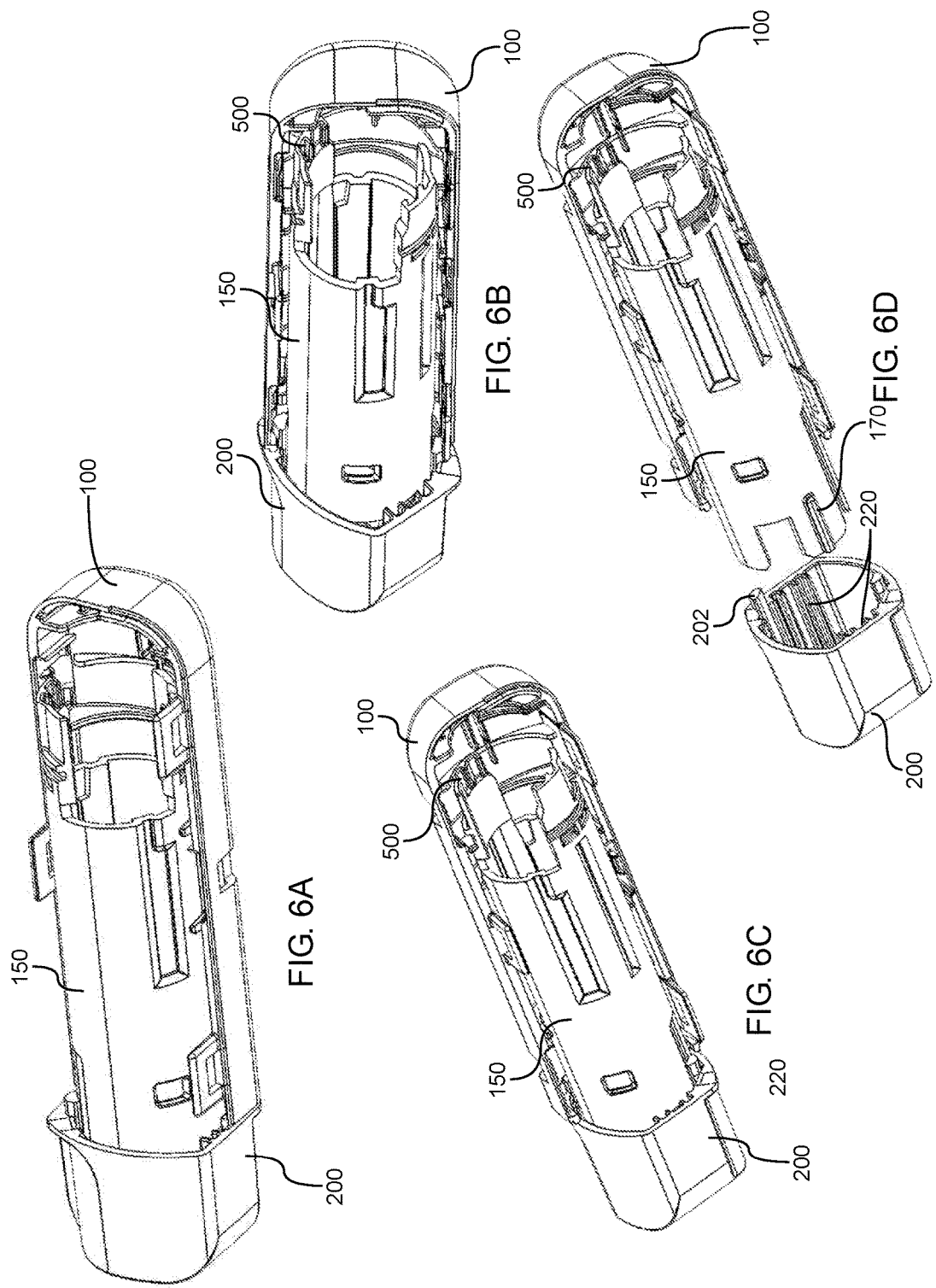

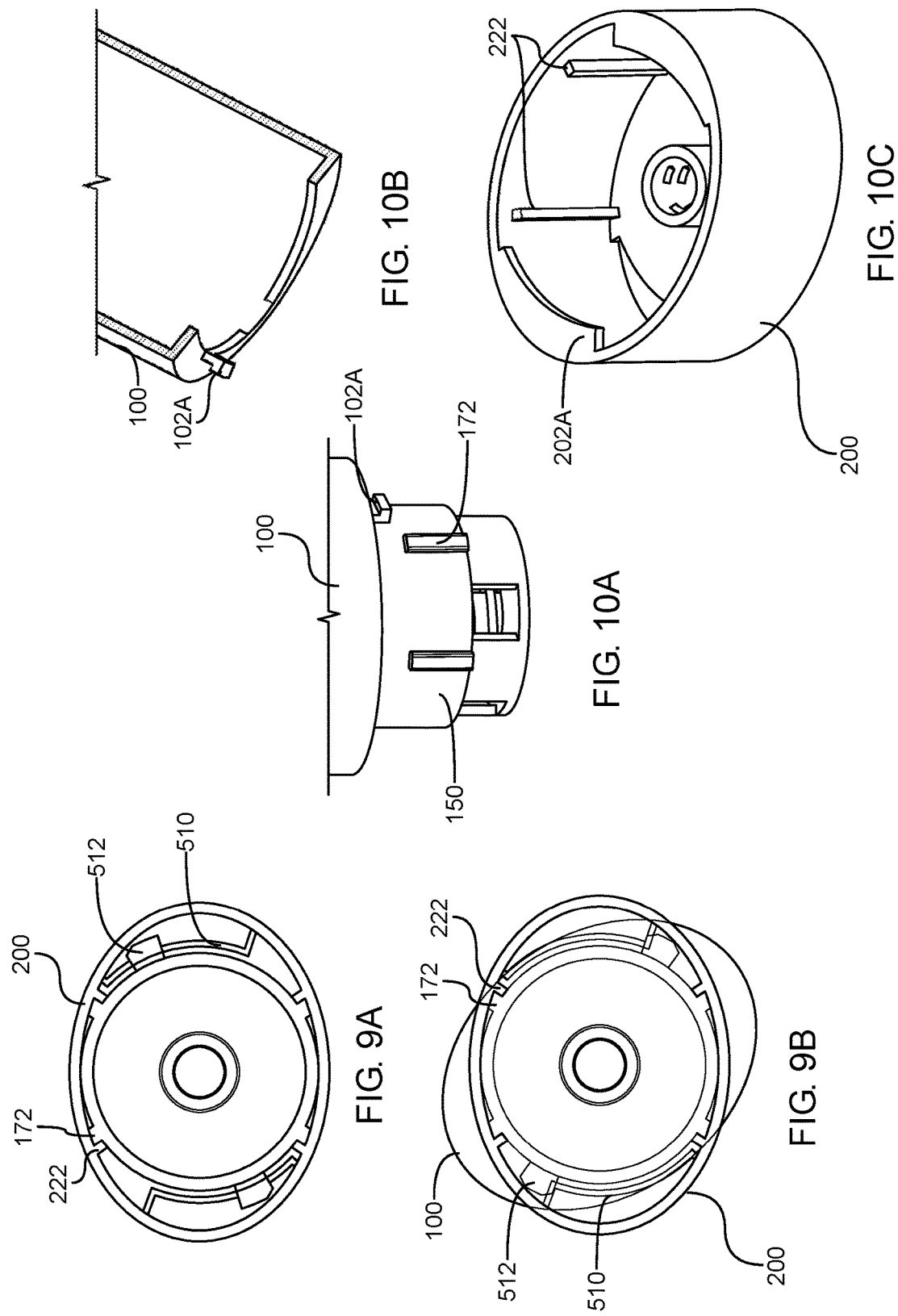

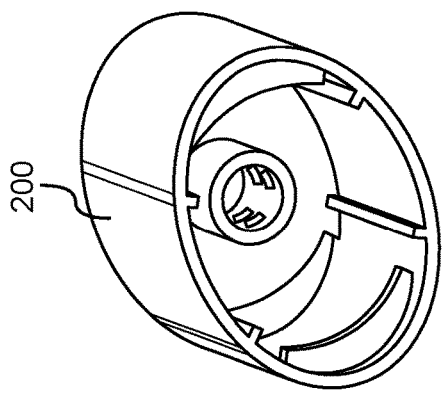
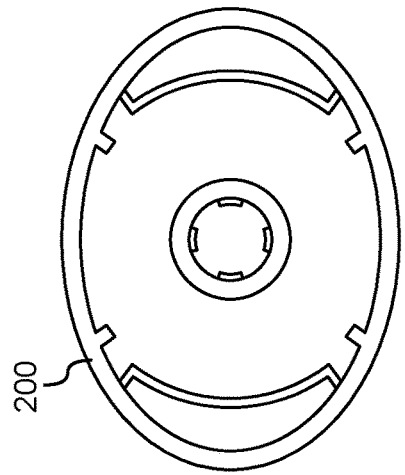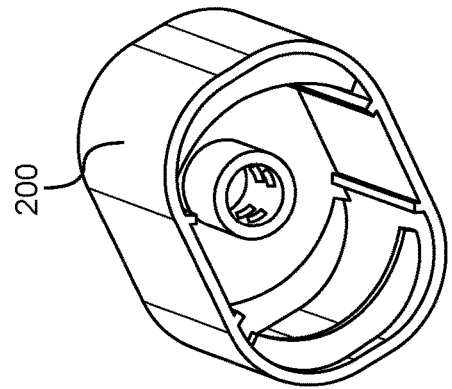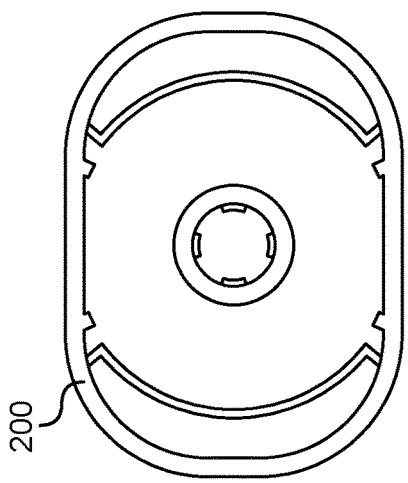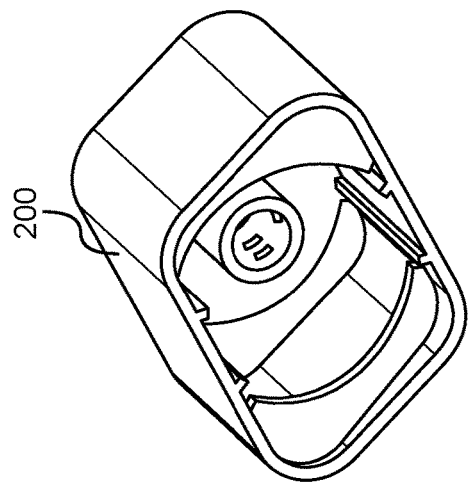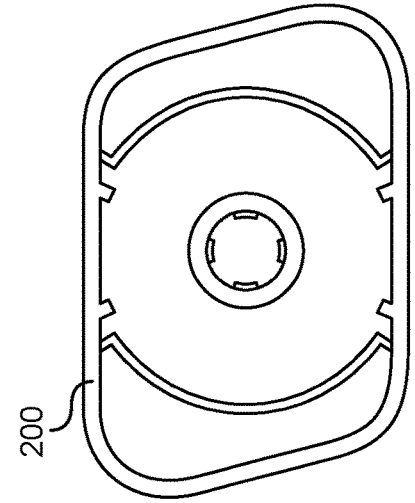

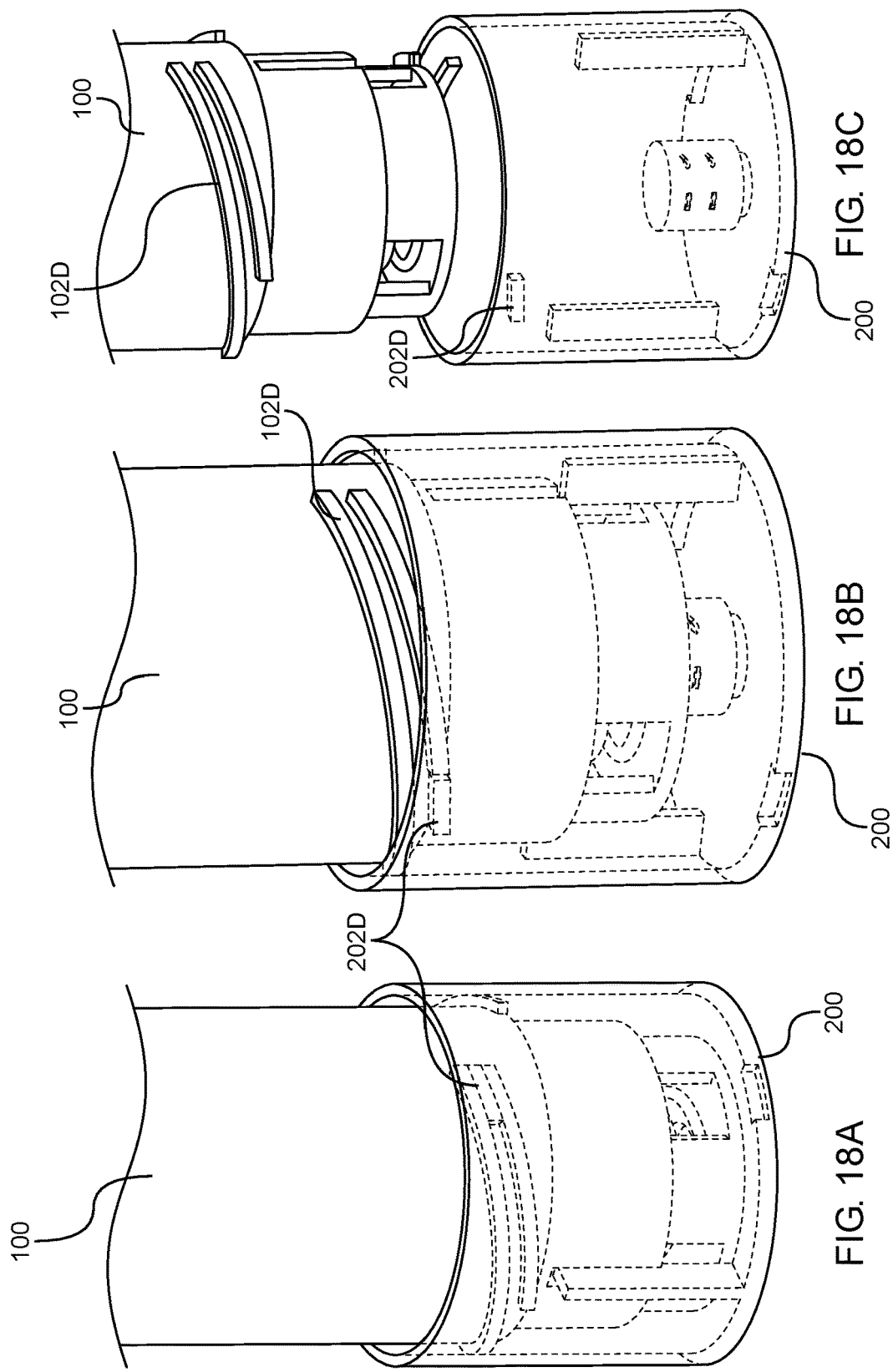

REMOVABLE ACTUATING CAP FOR USE WITH AN AUTO-INJECTOR ASSEMBLY

CROSS-REFERENCE TO RELATED APPLICATIONS

This application claims the benefit of U.S. Provisional Patent Application No. 62/147,958 which was filed on Apr. 15, 2015 which is herein incorporated by reference in its entirety.

FIELD OF THE INVENTION

The present invention relates generally to auto-injectors and prefilled syringes and more particularly to auto-injectors that store in a compact state and allow for formation or reconstitution of a therapeutic agent for injection.

BACKGROUND

It has been recognized that the shelf-life of the medications can be increased dramatically if the drug is stored as a dry medication. In addition, it is often that these medications are deployed in emergency situations where self-administration is preferred. In such emergency situations, the various actuation and mixing steps need to be performed in an intuitive manner such that they can be performed reliably in emergency situations with minimal complexity. For this reason it would be useful to have an easy-to-use auto-injector or a syringe-type device that automates the drug preparation process while also providing a platform which requires minimal user training and opportunity for user failure or dosing inaccuracy.

The invention here describes an interface whereby a single user input, involving removal of the cap, sets off a cascade of mechanical functions that initiates mixing, signals the completion of mixing, and places the device into an injection-ready state.

SUMMARY OF THE INVENTION

The device and systems of the invention contained in this disclosure include an auto-injector type mixing device, wherein the auto-injector includes a housing and a frame being rotatably disposed within the housing. The frame can be configured to carry a mixing assembly being disposed within the frame, wherein rotation of the frame within the housing can be configured to actuate the mixing assembly. The auto-injector can further include an injection assembly as well as a trigger assembly configured to actuate and cause extension of the injection assembly from within the auto-injector. A cap can also be provided which can be disposed about a distal end of the housing over the trigger assembly and the injection assembly, the cap being operatively connected to the housing on an interior portion, wherein rotation of the cap with respect to the housing imparts a relative rotation between the frame and the housing thus actuating the mixing assembly.

In some additional embodiments the cap can further include one or more interior channels being aligned axially, and wherein the frame further comprises an exterior protrusion corresponding in shape to the interior channel of the cap, wherein the interior channel and exterior protrusion are configured to allow an axial relative translation, but are constrained in a rotational degree of motion.

In various alternative embodiments the cap can also include one or more protrusions, and wherein the housing further comprises a corresponding lip about a distal end, wherein the one or more protrusions of the cap engage the lip in a stowed and intermediate state, and wherein the protrusions disengage from the lip at a mixed state, wherein rotation of the cap relative to the housing causes the device to move from the stowed state, through the intermediate state, and into the mixed state, whereupon the cap is configured to release, and be removed from the housing. In some such embodiments the one or more engagement lips can be ramped in an axial direction so as to allow travel between the cap and the housing in response to rotation.

In yet additional alternative embodiments the cap can also include a spring being configured to assist in separation of the cap from the housing after actuation.

In yet additional alternative embodiments the cap can be configured to include one or more engagement lips on an interior surface, and wherein the housing comprises one or more corresponding protrusions about a distal end, wherein the one or more protrusions of the housing engage the one or more engagement lips in a stowed and intermediate state, and wherein the one or more protrusions disengage from the one or more engagement lips at a mixed state, wherein rotation of the cap relative to the housing causes the device to move from the stowed state, through the intermediate state, and into the mixed state, whereupon reaching the mixed state the cap is configured to release, and be removed from the housing.

In yet additional alternative embodiments the cap can be configured to include a plurality of threads on an interior surface, and wherein the housing is provided with a plurality of corresponding threads on an exterior surface, and wherein rotation of the cap relative to the housing causes the device to move from a stowed state, through an intermediate state, and into a mixed state, whereupon reaching the mixed state the cap is configured to release, and be removed from the housing.

In yet additional alternative embodiments the cap and the housing can be configured to have a corresponding cross-sectional shape. In some such embodiments this cross-sectional shape can be an elliptical cross-sectional shape.

In yet additional alternative embodiments the mixing device can be configured to include a locking mechanism, the locking mechanism being configured to prevent the cap from rotating back into an aligned state indicative of a stowed state after an initial relative rotation between the cap and the housing.

Also included herein are methods of mixing a medication in a mixing device comprising the steps of rotating a cap relative to a housing, wherein an internal protruding component of the cap triggers an actuating component upon being rotated, wherein the actuating component causes separated medicament components to be combined in a chamber stored within the housing.

This method can further include releasing energy from a pre-stored energy component disposed when triggering the actuating component.

The method can also include an internal frame disposed within the housing that interacts and rotates with the internal protruding component.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIG. 4 illustrates side exterior perspective view of the medication mixing device of FIG. 3 with the cap rotated for an internal view;

FIGS. 5A-D illustrate various interior perspective views of the mixing subassembly where a portion of the housing is removed along with the internal frame 150 through various actuation steps moving from a stowed state to a mixed state;

FIGS. 6A-D illustrate various interior perspective views of the mixing subassembly showing the internal frame 150 interacting with the cap through various actuation steps moving from a stowed state to a mixed state;

FIGS. 9A-B illustrate another embodiment showing a cutaway view of the cap showing misalignment between cap and housing when rotated relative to each other in addition to a rotational locking mechanism;

FIGS. 10A-C illustrate an alternative embodiment of a mixing device where protruding engagement members extend into the cap from the frame and/or housing;

FIGS. 15A-17B illustrate various exterior perspective and internal views of various cap shapes;

FIGS. 18A-C illustrate various views of a cap provided with a plurality of threads that correspond to a plurality of corresponding threads.

DETAILED DESCRIPTION

It will be appreciated by those having skill in the area of fabrication and storage, and delivery of drugs, that the lifespan and effectiveness of the drug can be increased substantially by keeping the medication in a dry state. Storage in a dry state also decreases the rate of degeneration as well as the degenerative effects of temperature, for example heat exposure. By keeping the drug in a dry state the breadth of environments where the device can be stored is increased while decreasing the frequency of required replacement.

Figure 2A:
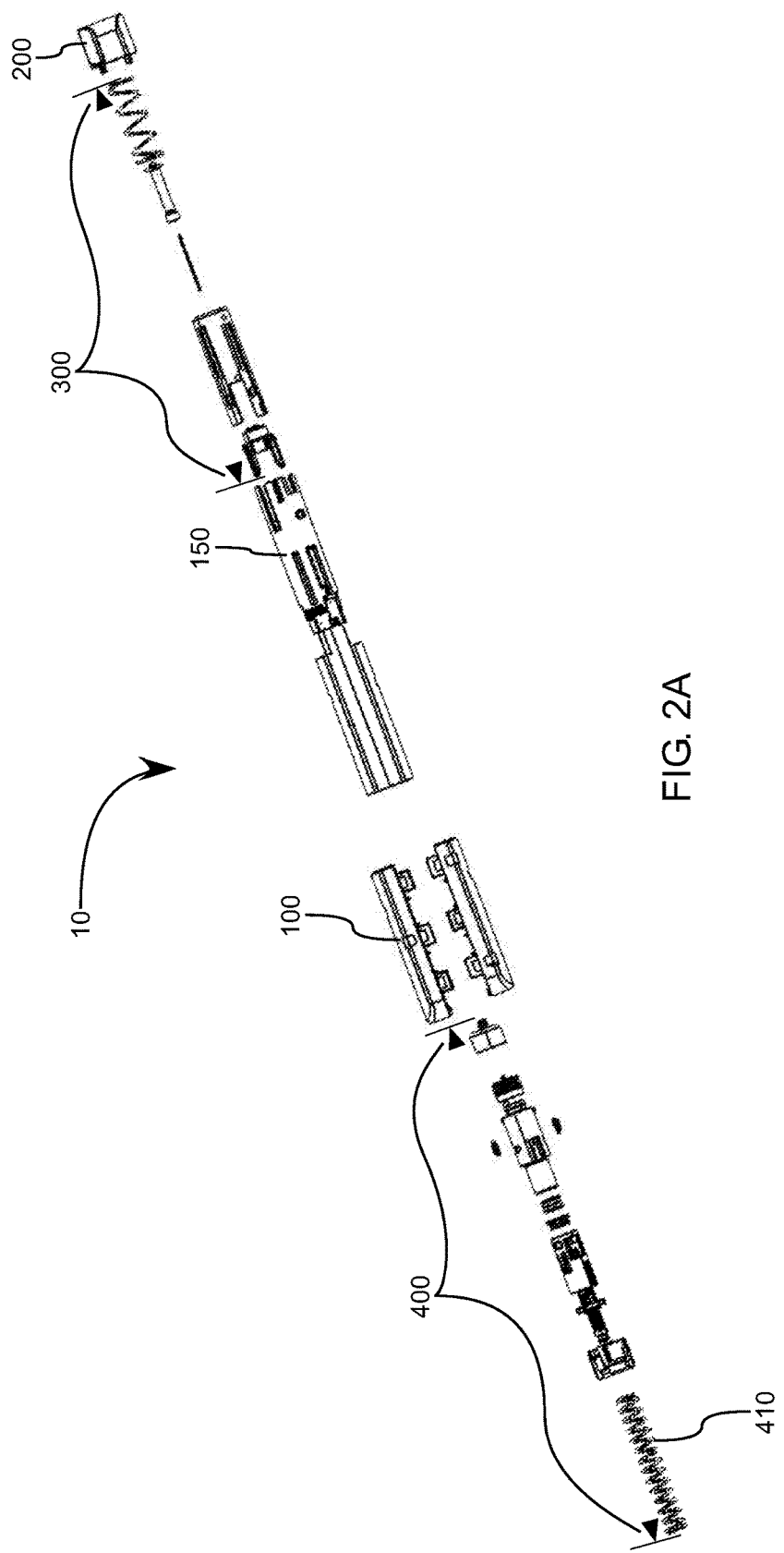
FIGS. 2A-B illustrate perspective exploded views of the medication mixing and delivery device and a mixing subassembly in accordance with the embodiment of FIGS. 1 A-C.
Figure 2B:
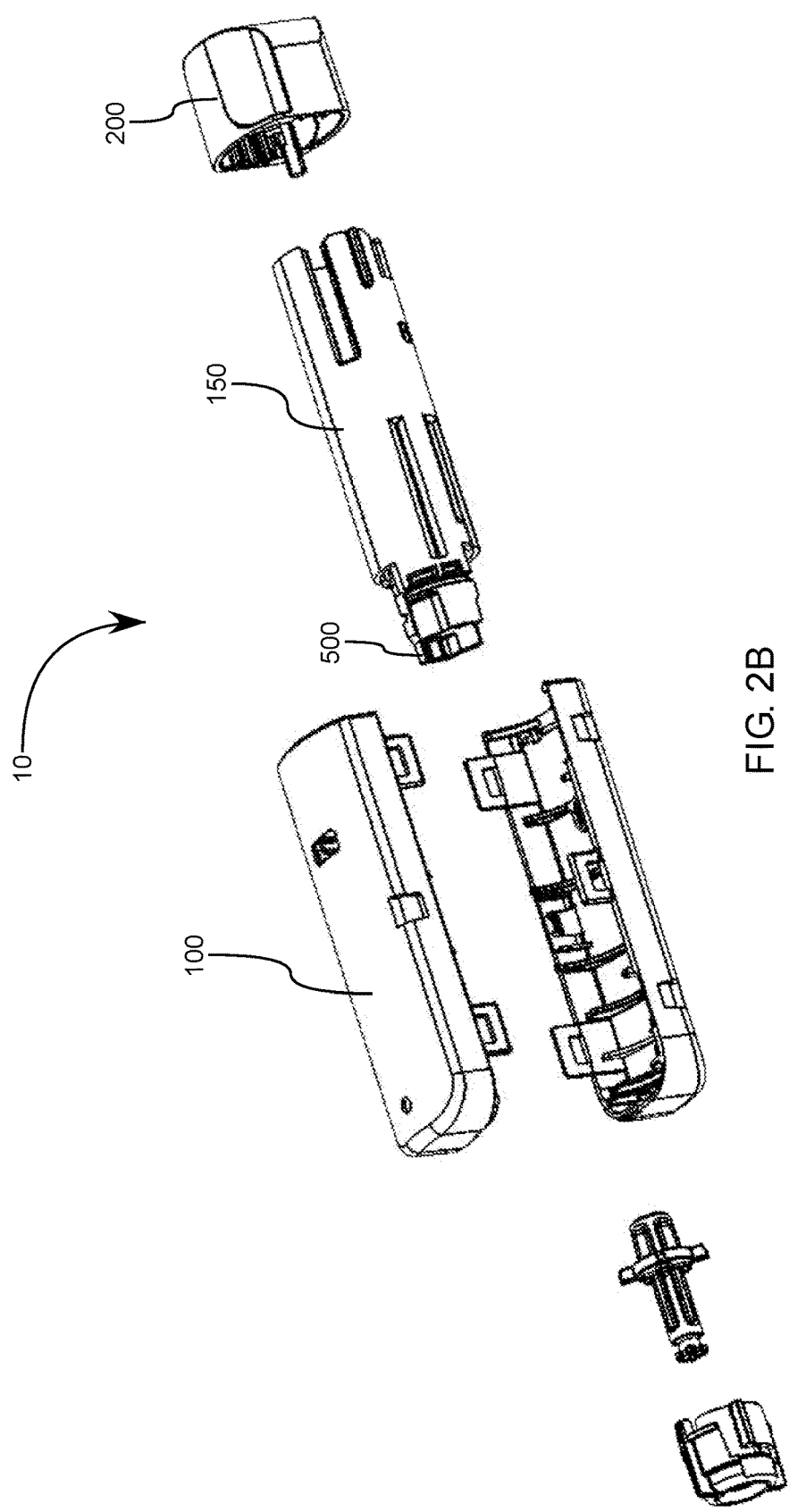
Figure 3:
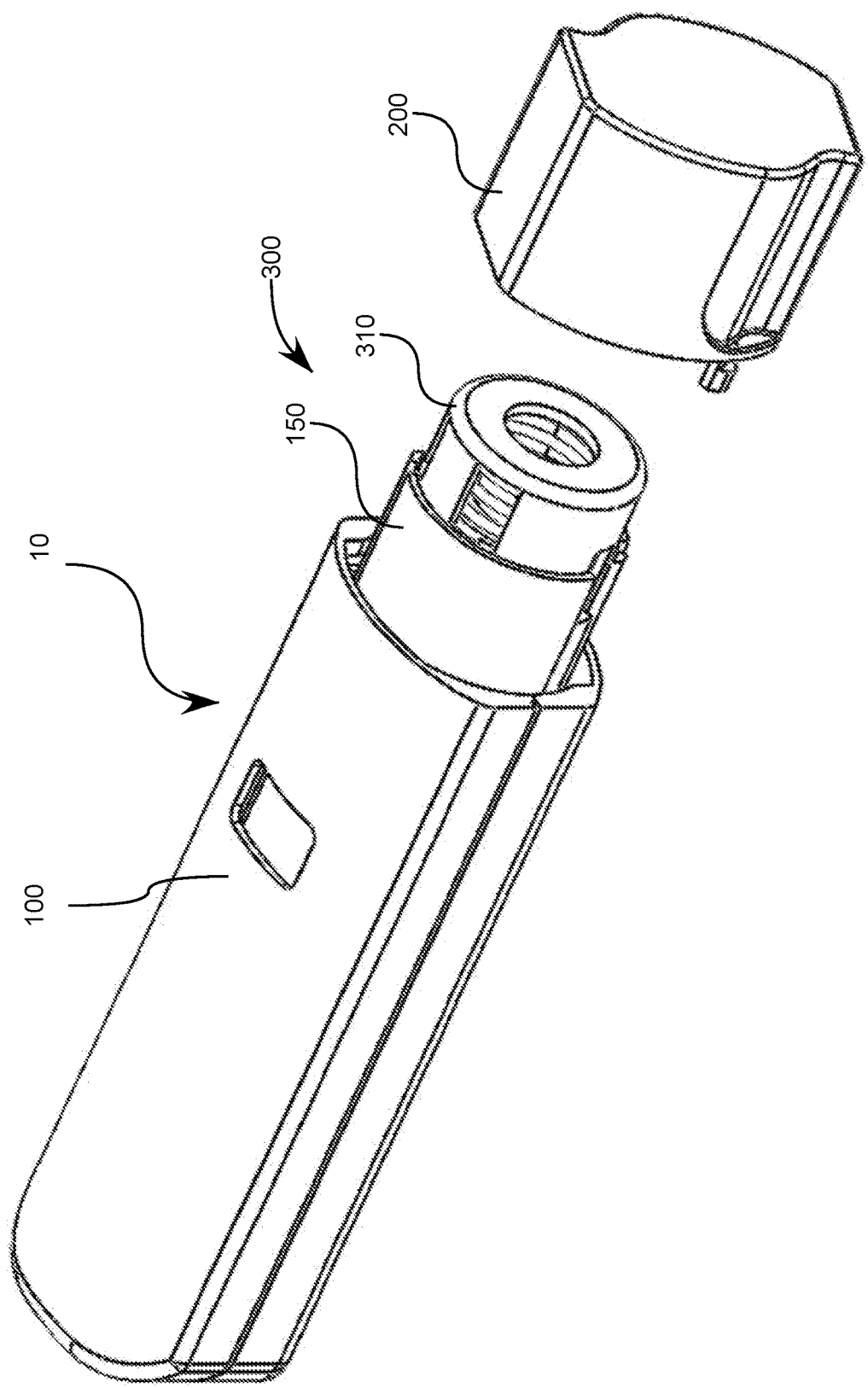
FIG. 3 illustrates a side exterior perspective view a medication mixing with the cap removed.
Figure 8A:
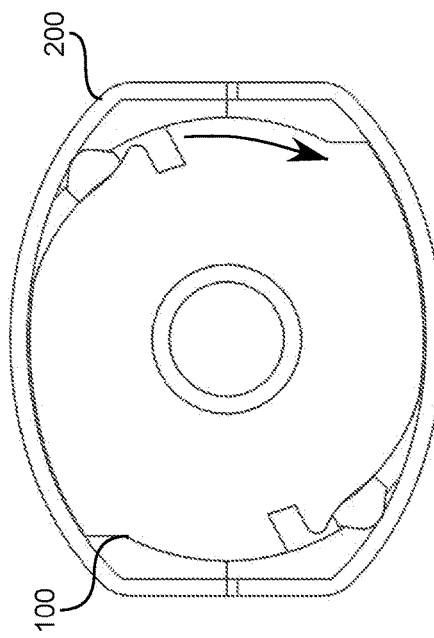
FIGS. 8A-B illustrates an embodiment showing misalignment of a cap and frame of the medication mixing device when the cap is rotated, where only the exterior wall of the cap is shown.
Figure 8B:
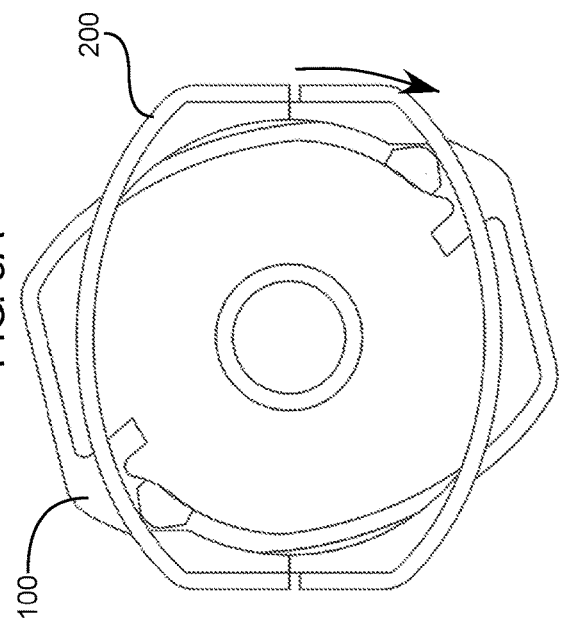
Figure 7:
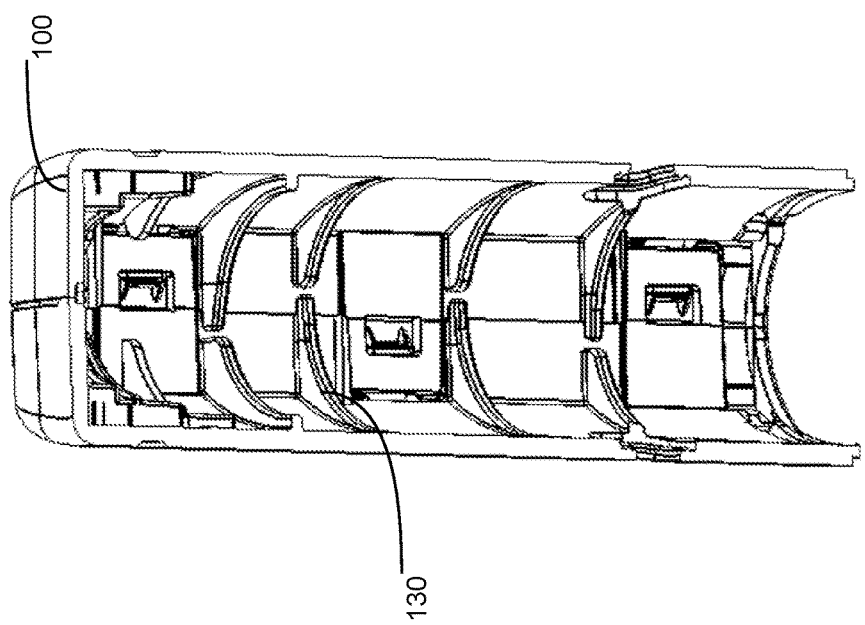
FIG. 7 illustrates an internal view of half of the housing 100 showing rails 103 about which an internal frame 150 can be positioned.

It should be noted that additional description of embodiments including pre-stored energy sources, illustrated herein as a spring 410, chambers, fluidic pathways, needles, medicaments, and other components are described in the following applications: U.S. App. No. 62/120,792 filed Feb. 25, 2015 and U.S. App. No. 62/126,011 filed Feb. 27, 2015 which are hereby incorporated by reference in their entirety. FIG. 2A illustrates an exemplary embodiment of an auto-injector having pre-stored energy sources, mixing components, injection assemblies, and actuation assemblies about which a rotational cap described herein can be integrated therewith.

The present invention illustrates various principles and devices which allow for the storage of a device having two or more components contained therein but which can quickly and reliably reconstitute, dissolve, fluidize, and/or put into a suspension, the components, i.e. mix them, immediately prior to delivery.

However, various issues can arise with drug mixing and delivery devices many of which will be addressed by the present invention as illustrated in the various embodiments. One such issue is that premature mixing of the drugs can also result in associated premature degradation of the drugs. In the present embodiments there are several types of sealing systems which exist between various drugs and/or chambers within the device. These barriers or seals are removed, destroyed, or somehow overcome in the actuation process prior to injection. As such it is desirable to provide indicators or other mechanisms which signal to the user that these barriers or seals remain intact.

In various embodiments the cap is provided at an injection end of the auto-injector. The rotating cap can be configured so as to couple to the auto-injector and provide a seal around an injection assembly and prevent contamination of the injection assembly thus maintaining the injection assembly in a sterile state, regardless of the environment in which it is kept, i.e. a backpack, pocket, purse, glove compartment of a car, etc.

Upon removal of the cap using one of the aforementioned embodiments, the injection assembly, which can involve the use of a bump switch, can be exposed, the needle can be extended, inserted into the patient, and the drug appropriately delivered.

Another issue addressed by the present invention is that the needle or injection assembly should not be exposed until the device is ready to inject. As discussed briefly above, auto-injectors are often used in emergency situations, such as to treat anaphylactic shock by mixing and delivering a dose of epinephrine. Or, using glucagon for treating hypoglycemia, sumatriptan for migraine headaches, diazepam for seizure medication, clotting factors for hemophilia, and so on. As such the atmosphere can be hectic and in order to reduce instances of premature activation of the injection assembly, loss of sterility by not properly cleaning a drug vial before manually drawing up a dose, or accidental unintentional sticks by the injection needle, the injection assembly, and associated needle, with an associated injection mechanism can be covered or shielded until the device is ready for injection, i.e. the drug has been completely mixed. In the present embodiment, the cap is configured to interact with actuation assemblies carried by the housing such that twisting and removal of the cap signal that the device is ready for injection.

Figure 1C:
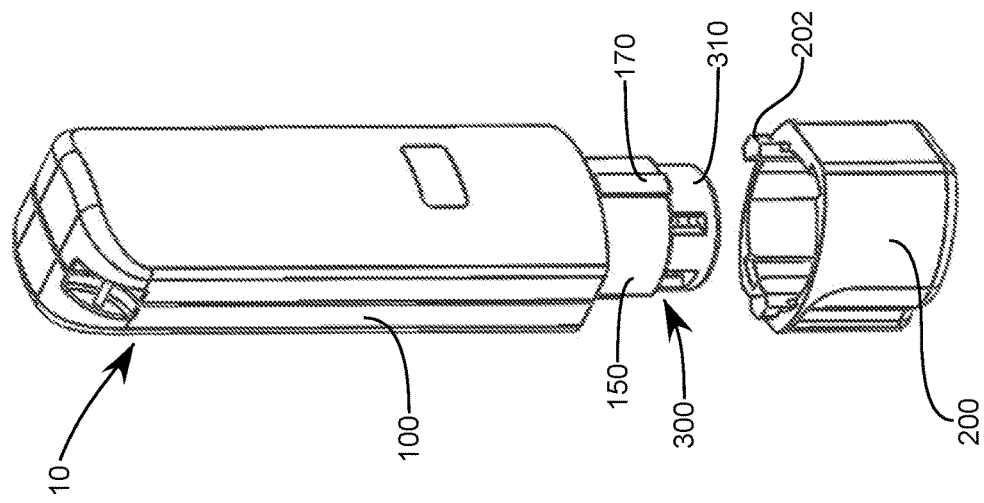
FIGS. 1A-C illustrate perspective exterior views of a medication mixing and delivery device through various actuation steps.
Figure 1B:
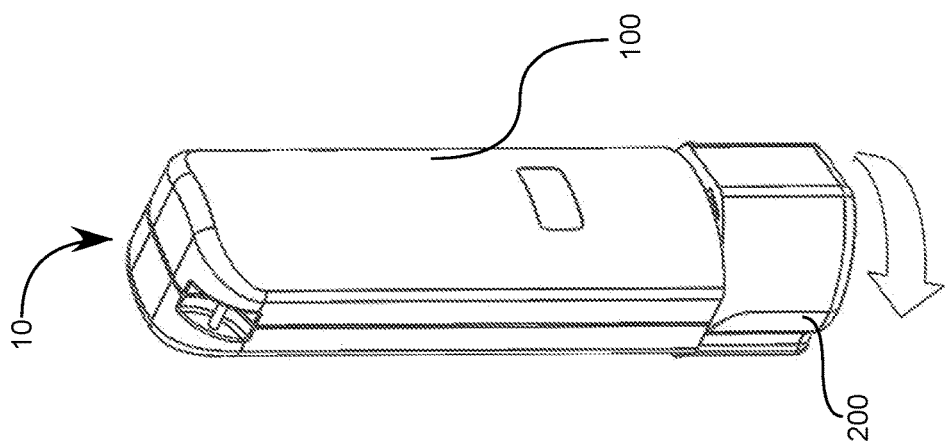
Figure 1A:
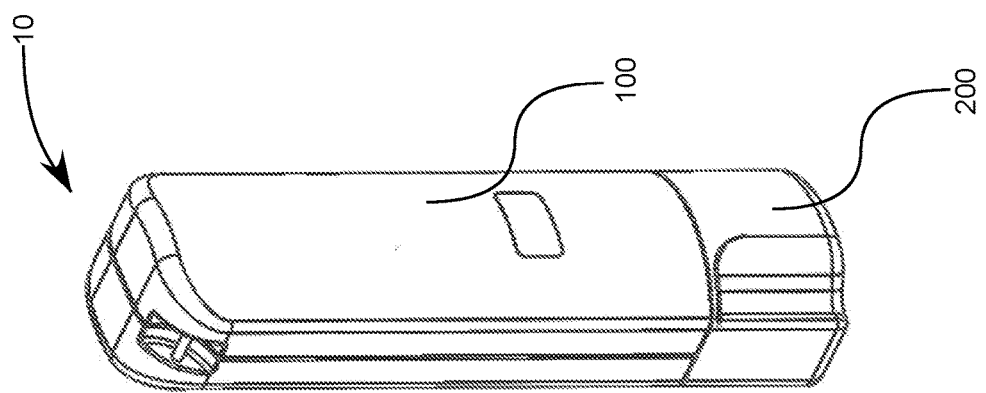

Yet another issue which is addressed by the various embodiments discussed herein involves the reduction of mandatory steps that need to be performed by the user. As discussed above, such high-intensity situations can result in an inability to remember numerous steps and as such removal of as any necessary steps and streamlining the activation process will be of great advantage in ensuring proper drug delivery. The devices of the present invention, and as illustrated in FIGS. 1A-C, illustrate various aspects of the present invention which involves providing an auto-injector 10 wherein FIG. 1A illustrates a stowed state. The injector 10 can include a housing 100 and a cap 200. Rotation of the cap 200 with respect to the housing 100 causes an actuation of an internal mixing assembly (not shown here) which activates the mixing of the various drugs contained within the housing. FIG. 1B illustrates a partial or intermediate relative rotation between the cap 200 and the housing 100. FIG. 1C illustrates a full rotation wherein the cap 200 is released from the housing 100 thus signaling that the mixing step has begun, and readying the device for injecting the mixed medicament components. Other indicators can be provided that indicate a fully-mixed state, provide visibility on the mixed drug, and then allow exposure of an injection assembly 300 and the injection trigger, i.e. the switch 310 to be triggered. At this point the device can be pressed against an injection site, i.e. the skin of the patient, the injection trigger, i.e. the switch 310 will be pressed upward into the housing 100 and the injection assembly 300 can extend a needle (not shown here) and eject the now mixed drugs contained therein.

As shown in FIG. 1C, and FIGS. 3-6, the cap 200 can include one or more channels 220 which can be axially aligned, and are configured to correspond in shape with, as well as interact with, one or more axially aligned protrusions 170 provided on the frame 150. The channels 220 and the protrusions 170 act as an internal cam system to rotate the frame 150 with respect to the housing 100 as the cap 200 is rotated, which in turn operates to open a valve or otherwise allow for mixing of various drugs contained within the housing. For example, a valve can be opened and a displacement mechanism released which allows a wet solvent to flow into and dissolve a dry drug contained in a secondary dry chamber. It will be appreciated that by aligning the channels and the protrusions in an axial manner, the cap will be capable of sliding axially with respect to the frame, which will be necessary for removal of the cap upon completion of the necessary rotation for actuation.

In some embodiments, and as seen in FIGS. 1C, 2B, 3-6, the cap 200 can further include one or more protrusions 202, and wherein the housing 100 can further include a corresponding lip 102 about a distal or injection end, wherein the one or more protrusions 202 of the cap 200 can be configured to engage the corresponding lip 102 in a stowed and intermediate state, as shown in FIGS. 1A and 1B respectively, and wherein the protrusions 202 disengage from the corresponding lip 102 at a mixed state, as shown in FIG. 1C.

It will be appreciated that in order to facilitate release upon completion of the mixing, the corresponding lip 102 can be provided with a release channel or cutout 104 which at a relative radial rotation allows for the cap 200, and protrusions 202, to disengage from the housing 100 and corresponding lip 102 so as to expose the injection assembly 300 and injection trigger, i.e. the switch 310.

It will be appreciated that in certain instances the user will desire some sort of an indication that the device is responding to user input and is performing the requisite internal functions, and that mere removal of the cap may, in some instances be insufficient indication of such functionality. As such, in some embodiments, and as shown in FIGS. 12-14 and 18A-C, the one or more engagement lips 102 B-D can be provided in an axially ramped configuration being engaged with internal protrusions 202 B-D extending from the cap 200 wherein relative rotation between the cap 200 and the housing 100 results in an axial translation or travel between the cap 200 and the housing 100. This axial translation results in a manual separation between the cap and the housing which provides a gap 600 which provides some measure of tactile or even visual indication to the user that the rotational input provided between the housing and the cap is providing the desired internal functionality, i.e. that mixing is actually occurring. In some embodiments, the gap 600 which is generated between the cap 200 and the housing 100 can be provided with additional visual or tactile indicia which provide confirmation of internal operations. In some embodiments an underlying color band can be provided on the housing 100 as the cap translates respective to the housing, wherein the color band is initially hidden by the cap in the stowed state, wherein the gap 600 provides visibility of the color band, which increases throughout relative rotation therebetween.

It will be appreciated that FIGS. 10A-C illustrate how the cap and the frame can have the axial protrusions and channels reversed wherein the channels 172 are provided on the frame 150 with corresponding internal protrusions 222 provided in the cap 200. FIGS. 10A-C also illustrates how the retention mechanisms can be reversed wherein tabs 102A can be provided on the housing 100 which engage a corresponding lip 202A provided on the cap 200.

In yet additional embodiments, and as shown in FIG. 4, the cap 200 can be provided with a spring 250 which is configured to aid or otherwise assist in separation of the cap 200 from the housing 100 upon completion of the requisite relative rotation between the cap 200 and the housing 100 so as to signal completion of the actuation of the mixing by the mixing assembly, 400 (as shown in FIG. 2A), wherein the spring provides a separation force and causes the cap 200 to separate from the housing 100 upon completion of the required relative rotation absent a pulling or tensile force input by the user. This is achieved because the spring cannot overcome the tensile strength of the protrusions and corresponding lip discussed above until the protrusions 202 are aligned with the separation channel 104 (see FIG. 5B, 5D) at a desired relative rotational position between the cap 200 and the housing 100.

In some alternative embodiments, and as shown in FIGS. 10A-C, the engagement components of the cap 200 and the housing 100, can be reversed, with respect to the embodiments discussed above. In this embodiment the cap 200 can instead include one or more engagement lips 202A on an interior surface, and the housing 100 can instead include one or more corresponding protrusions 102A about a distal end. In this embodiment the one or more protrusions 102A of the housing 100 engage the one or more engagement lips 202A in a stowed and intermediate state, and wherein the one or more protrusions 102A disengage from the one or more engagement lips 202A at a mixed state, wherein rotation of the cap 100 relative to the housing causes the device to move from the stowed state, through the intermediate state, and into the mixed state, whereupon reaching the mixed state the cap is configured to release, and be removed from the housing.

In yet additional embodiments, and as shown in FIGS. 18A-C the cap 200 can be provided with a plurality of threads 102D on an interior surface, and wherein the housing 100 is provided with a plurality of corresponding threads 102D on an exterior surface, and wherein rotation of the cap relative to the housing causes the device to move from a stowed state, through an intermediate state, and into a mixed state, whereupon reaching the mixed state the cap the relative threads are configured to release, and the cap 200 release so as to be removed from the housing 100.

FIGS. 15A-17B illustrate how the housing 100 and the cap 200 can have varying cross-sectional shapes, wherein the cross-sectional shape of the housing 100 and the cap 200 correspond to one another. It will be further appreciated that the corresponding nature of the relative shapes can be properly aligned and flush in the stowed state. However, the variation of the cross-sectional shape renders any relative rotation between the cap 200 and the housing 100 particularly obvious, as any rotation would result in readily apparent misalignment, both in a tactile and visual sense. FIGS. 8A-9B help illustrate this visual and tactile misalignment between cap and housing.

Additionally, an elliptical cross-sectional shape allows for easier assembly when initially preparing the device as the space between the major and minor radii allows for access, depression of, and engagement of various assembly tools, locking mechanisms, etc.

As discussed briefly above, it will be appreciated, that any rotation out of the stowed and aligned state may result in a partial removal or overcoming of barriers or seals in place to keep the various drug components separated, wherein any mixing thereof would likely accelerate the degradation process and thus render the drugs inert or contaminated. As such a locking mechanism can be provided to the device which prevents any backward rotation after an initial rotation between the cap and the housing. One such embodiment of a locking mechanism is illustrated in FIGS. 6B-D and FIGS. 11A-C. The locking mechanism 500 can be provided as a series of ratcheting protrusions 520 which engage a corresponding protrusion 132, as seen in FIGS. 11A-C, in the frame 150 or housing 100. In this manner, as the frame 150 rotates with respect to the housing 100, and stationary plunger and protusion 132, in response to a torsional force between the cap 200 and the housing 100, the ratchet engages and allows movement is one relative rotational direction, but not backwards into a re-aligned state. In this manner once the cap 200 is rotated out of the stowed state, it cannot be returned to the stowed position by the user, thus signaling that the drugs contained therein may have been compromised, and the device needs to be replaced.

Another embodiment of a locking mechanism is illustrated in FIGS. 9A-B wherein the cap itself is provided with a resilient ramped lock 510, which ramped lock can be disengaged during initial assembly, but upon initial rotation out of the stowed state engages a corresponding tab 512 or other protrusion on the frame or housing can be provided which prevents backward rotation back into the stowed state.

Figure 11:
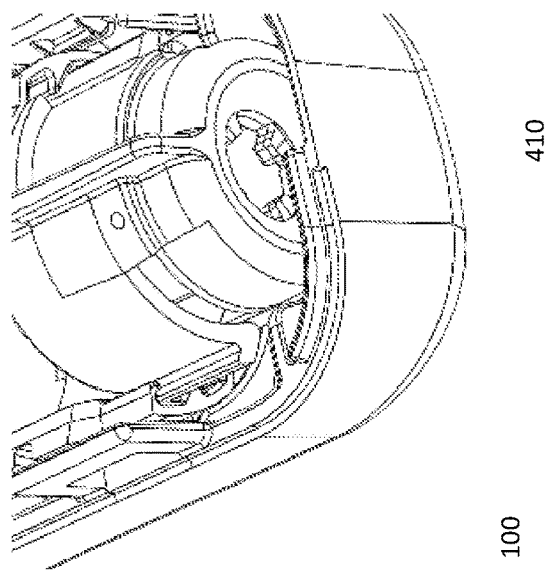
FIGS. 11A-C illustrate various perspective partially cutaway views of a cap locking mechanism for a mixing device triggered by a rotational cap.
Figure 11:
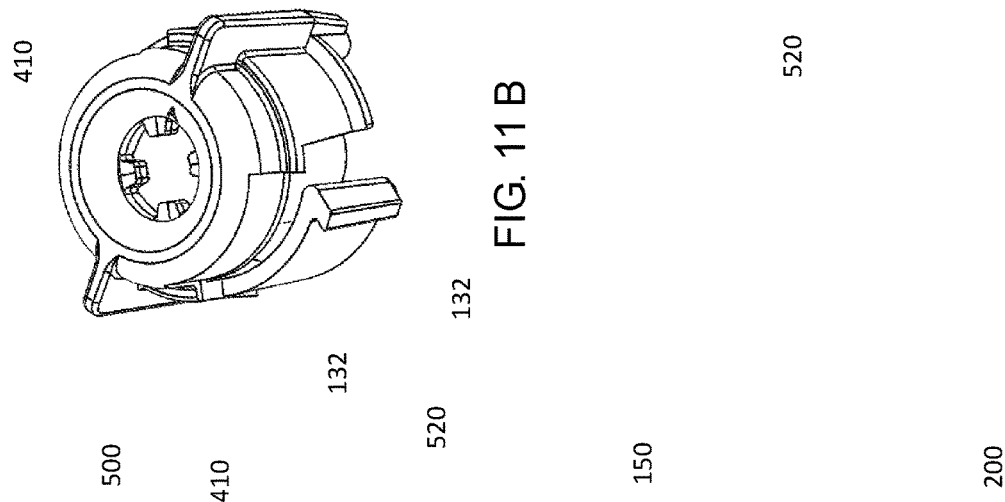
Figure 11:
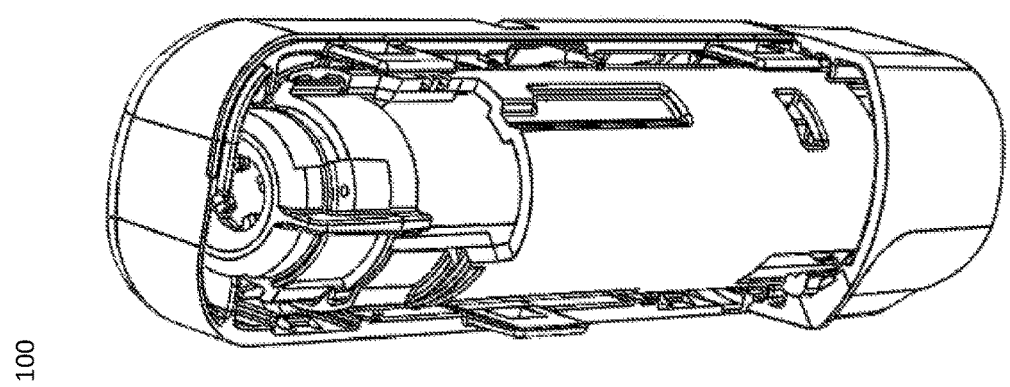
Figure 14:
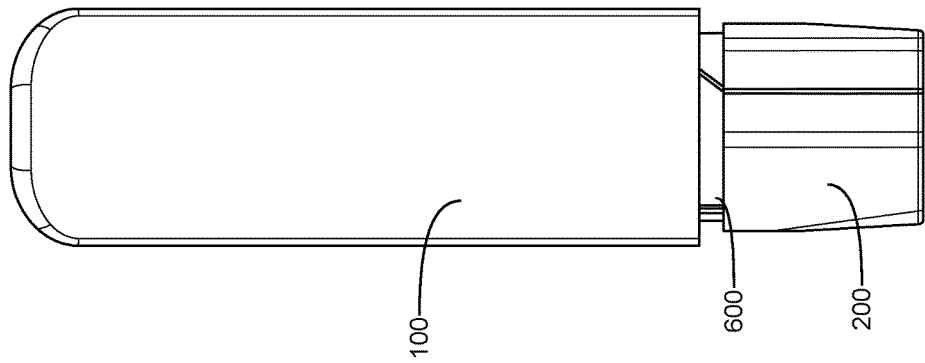
FIG. 14 illustrates the creation of a gap 600 when the cap is rotated with respect to a housing in some embodiments of the mixing device described herein.
Figure 12:
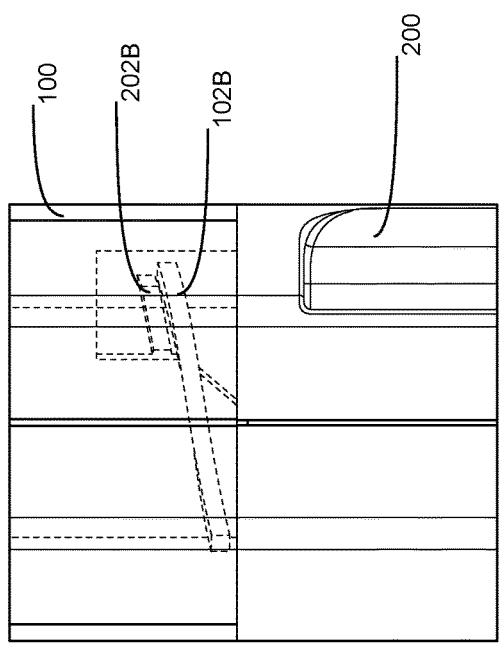
FIGS. 12-13 illustrate various embodiments of mixing devices having varying protrusions (202B-C) and corresponding lips in the cap (102B-C)
Figure 13:
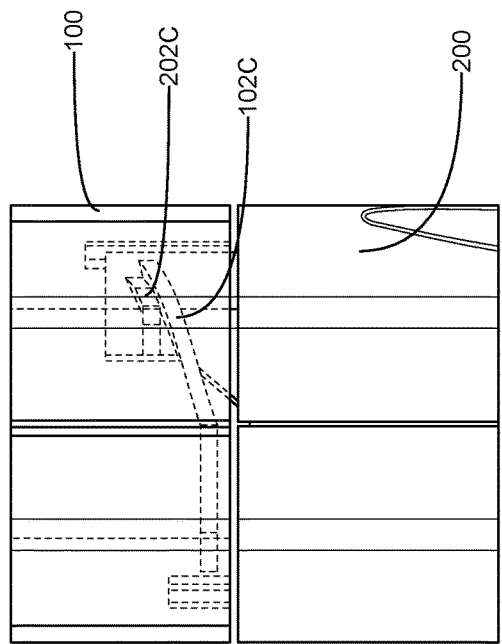

In yet additional embodiments, and as shown in FIG. 11, the locking mechanism 500 can be alternatively provided as a series of ratcheting protrusions 520 provided on the frame 150 can be interior facing and engage with a rotationally fixed plunger 410 device of the mixing assembly.

It will be appreciated that various cap shapes can be utilized, either circular or non-circular. Some advantage has been realized through the use of non-circular geometric shapes, and in particular ellipsoid cap. Ellipsoid shapes provide additional interior space between the major and minor diameters into which the tabs and corresponding locking grooves can be formed. In addition to providing additional interior space, the relative rotation between the cap 200 and the frame of the drug mixing system results in a visible change in relative position, as the edges will change respective position with respect to one another continuously through the rotational distance as the cap is twisted.

It will also be appreciated that a rotational distance, i.e. a distance the cam is required to move in order to fully activate or open the valve, can be adjusted to be virtually any fixed value. However, it has been recognized, particularly with respect to ellipsoid shapes that a relative rotational distance from 35-90 relative degrees is preferred because at 90 degrees the two ellipsoid shapes will be the furthest out of phase which can signify a complete opening before the two shapes begin to move back into phase and can give the mental impression that the valve is moving back to closed.

It will also be appreciated that the cross sectional area of the frame 150 can be provided as circular, wherein the circular cross-section of the frame 150 rides or engages a series of interior rails 130 of the housing 100 which rails 130 provide an effectively circular interior profile to the housing 100 and allow for free rotation, upon actuation, between the frame 150 and the housing 100.

It should be noted that other user interface components or systems may be used that may not exactly be caps as shown in several of the embodiments, but include similar rotational, pull-away, interfacing components that are in communication with the main housing of the mixing and/or injection device. One purpose of these interface components is to function as an initiating step to begin a mixing process. Another purpose is to allow the devices to be transformed from a non-ready to ready state. Other purposes will be apparent to those skilled in the art.

These embodiments and features illustrated and described herein are exemplary but not intended to be limiting nor are the claims listed at the end of this application. Multiple combinations and equivalent component parts are considered within the scope of this application.

The invention claimed is:

1. A mixing device comprising:
   a housing;
   a frame being rotatably disposed within the housing;
   a mixing assembly being disposed within the frame, the mixing assembly being configured to actuate in response to rotation of the frame with respect to the housing;
   an injection trigger; and
   a cap being disposed at a distal end of the housing over the injection trigger, the cap being operatively connected to an interior portion of the housing, wherein rotation of the cap with respect to the housing imparts a relative rotation between the frame and the housing thus actuating the mixing assembly.

2. The mixing device of claim 1, wherein the cap further comprises an interior channel being aligned axially, and wherein the frame further comprises an exterior protrusion corresponding in shape to the interior channel of the cap, wherein the interior channel and exterior protrusion are configured to allow an axial relative translation, but are constrained in a rotational degree of motion.

3. The mixing device of claim 1, wherein the cap further comprises one or more protrusions, and wherein the housing further comprises a corresponding lip about a distal end, wherein the one or more protrusions of the cap engage the lip in a stowed and intermediate state, and wherein the protrusions disengage from the lip at a mixed state, wherein rotation of the cap relative to the housing causes the device to move from the stowed state, through the intermediate state, and into the mixed state, whereupon the cap is configured to release, and be removed from the housing.

4. The mixing device of claim 3, wherein the one or more engagement lips are ramped in an axial direction so as to allow travel between the cap and the housing in response to rotation.

5. The mixing device of claim 3, wherein the cap further comprises a spring configured to assist in separation of the cap from the housing after actuation.

6. The mixing device of claim 1, wherein the cap further comprises a one or more engagement lips on an interior surface, and wherein the housing comprises one or more corresponding protrusions about a distal end, wherein the one or more protrusions of the housing engage the one or more engagement lips in a stowed and intermediate state, and wherein the one or more protrusions disengage from the one or more engagement lips at a mixed state, wherein rotation of the cap relative to the housing causes the device to move from the stowed state, through the intermediate state, and into the mixed state, whereupon reaching the mixed state the cap is configured to release, and be removed from the housing.

7. The mixing device of claim 1, wherein the cap is provided with a plurality of threads on an interior surface, and wherein the housing is provided with a plurality of corresponding threads on an exterior surface, and wherein rotation of the cap relative to the housing causes the device to move from a stowed state, through an intermediate state, and into a mixed state, whereupon reaching the mixed state the cap is configured to release, and be removed from the housing.

8. The mixing device of claim 1, wherein the cap and the housing have a corresponding cross-sectional shape.

9. The mixing device of claim 1, wherein the mixing device further comprises a locking mechanism, the locking mechanism configured to prevent the cap from rotating back into an aligned state indicative of a stowed state after an initial relative rotation between the cap and the housing.

10. A mixing device comprising:
  a housing;
  a frame being rotatably disposed within the housing;
  a mixing assembly being disposed within the frame, the mixing assembly being configured to actuate in response to rotation of the frame with respect to the housing;
  an injection trigger; and
  a cap being disposed at a distal end of the housing over the injection trigger, the cap being operatively connected to the housing on an interior portion, wherein rotation of the cap with respect to the housing imparts a relative rotation between the frame and the housing, thus actuating the mixing assembly;
  wherein the cap and the housing have a corresponding cross-sectional shape; and
  wherein rotation of the cap causes the mixing device to change from a stowed, through an intermediate state, and into a fully mixed state.

11. The mixing device of claim 10, wherein the cap further comprises an interior channel being aligned axially, and wherein the frame further comprises an exterior protrusion corresponding in shape to the interior channel of the cap, wherein the interior channel and exterior protrusion are configured to allow an axial relative translation, but are constrained in a rotational degree of motion.

12. The mixing device of claim 10, wherein the cap further comprises one or more protrusions, and wherein the housing further comprises one or more corresponding lips about a distal end, wherein the one or more protrusions of the cap engage the lip in a stowed and intermediate state, whereupon reaching the fully mixed state the cap is configured to release, and be removed from the housing thus.

13. The mixing device of claim 12, wherein the one or more corresponding lips are ramped in an axial direction so as to allow travel between the cap and the housing in response to rotation.

14. The mixing device of claim 12, wherein the cap further comprises a spring configured to assist in separation of the cap from the housing after actuation.

15. The mixing device of claim 10, wherein the cap further comprises a one or more engagement lips on an interior surface, and wherein the housing comprises one or more corresponding protrusions about a distal end, wherein the one or more protrusions of the housing engage the one or more engagement lips in a stowed and intermediate state, and wherein the one or more protrusions disengage from the one or more engagement lips at the fully-mixed state, whereupon reaching the fully-mixed state the cap is configured to release, and be removed from the housing.

16. The mixing device of claim 10, wherein the cap is provided with a plurality of threads on an interior surface, and wherein the housing is provided with a plurality of corresponding threads on an exterior surface, whereupon reaching the fully-mixed state the cap is configured to release, and be removed from the housing.

17. The mixing device of claim 10, wherein the mixing device further comprises a locking mechanism, the locking mechanism configured to prevent the cap from rotating back into an aligned state indicative of a stowed state after an initial relative rotation between the cap and the housing.

18. A mixing device comprising:
  a housing;
  a frame being rotatably disposed within the housing;
  a mixing assembly being disposed within the frame, the mixing assembly being configured to actuate in response to rotation of the frame with respect to the housing; and
  a cap being disposed at a distal end of the housing, the cap being operatively connected to the housing on an interior portion, wherein rotation of the cap with respect to the housing imparts a relative rotation between the frame and the housing, thus actuating the mixing assembly.

19. The mixing device of claim 18 further comprising:
  the housing having one or more engagement lips about a distal end;
  the frame further comprises an exterior protrusion corresponding in shape to an interior channel of the cap;
  an injection assembly; and
  a locking mechanism, the locking mechanism configured to prevent the cap from rotating back into an aligned state indicative of a stowed state after an initial relative rotation between the cap and the housing;
  wherein the cap and the housing have a corresponding cross-sectional shape;
  wherein rotation of the cap causes the mixing device to change from the stowed, through an intermediate state, and into a fully mixed state.

20. A method of mixing a medication in a mixing device comprising the steps:
  rotating a cap relative to a housing, wherein an internal protruding component of the cap triggers an actuation upon being rotated by imparting rotation to a frame provided within the housing, wherein the actuation causes separated medicament components to be combined in a chamber stored within the housing.

21. The method of claim 20, wherein the triggering releases energy from a pre-stored energy component disposed within the housing.

22. The method of claim 20, wherein the internal protruding component interacts with a rotatable frame disposed within the housing.

* * * * *